United States Patent [19]

Werly

[11] Patent Number: 5,007,837

[45] Date of Patent: Apr. 16, 1991

[54] DIFFERENTIAL PHOTOPOLYMERIZATION PROCESS USED FOR FILLING A DENTAL CAVITY AND A TOOL INTENDED FOR ITS IMPLEMENTATION

[75] Inventor: Marc Werly, Paris, France

[73] Assignee: Ellena, Wissembourg, France

[21] Appl. No.: 172,562

[22] Filed: Mar. 24, 1988

[30] Foreign Application Priority Data

Mar. 26, 1987 [FR] France ................ 87 04230

[51] Int. Cl.[5] ................................ A61C 5/04
[52] U.S. Cl. ................................ 433/226; 433/29; 433/229
[58] Field of Search ............... 433/226, 228.1, 215, 433/29, 229, 141, 149

[56] References Cited

U.S. PATENT DOCUMENTS

| | | | |
|---|---|---|---|
| 4,064,629 | 12/1977 | Stoner et al. | 433/226 X |
| 4,608,021 | 8/1986 | Barrett | 433/215 X |
| 4,631,030 | 12/1986 | von Weissenfluh | 433/229 X |
| 4,666,405 | 5/1987 | Ericson | 433/228.1 X |
| 4,666,406 | 5/1987 | Kanca, III | 433/228.1 X |
| 4,673,353 | 6/1987 | Nevin | 433/229 X |
| 4,696,646 | 9/1987 | Maitland | 433/149 |
| 4,726,770 | 2/1988 | Kurer | 433/215 X |

*Primary Examiner*—Robert P. Swiatek
*Assistant Examiner*—Nicholas D. Lucchesi
*Attorney, Agent, or Firm*—Schwartz & Weinrieb

[57] ABSTRACT

The invention relates to a process for filling a cavity within a tooth or mold, and also to a tool intended for the implementation of the process.

The process, which is of the type in which a photosensitive resin intended to be solidified by means of photopolymerization is deposited within the cavity (3), is remarkable according to the invention in that a layer (8) of a first resin which is photosensitive at a first level of luminous radiation is deposited upon the walls (5, 6) of the cavity (3);

a mass (10) of a second resin which is photosensitive at a second level of luminous radiation is deposited upon the layer (8), effectively filling the rest of the cavity (3);

hardening is performed by means of the photopolymerization of the mass (10) by exposure to the second level of luminous radiation transmitted by means of a pellet (27) immersed within the mass (10);

and, after hardening of the mass (10), the hardening of the layer (8) of photosensitive resin is performed by means of exposure to the first level of luminous radiation, using the pellet (27).

Applications: dental treatment and care, and precision molding and casting.

11 Claims, 2 Drawing Sheets

DIFFERENTIAL PHOTOPOLYMERIZATION PROCESS USED FOR FILLING A DENTAL CAVITY AND A TOOL INTENDED FOR ITS IMPLEMENTATION

FIELD OF THE INVENTION

The present invention relates to a differential photopolymerization process with shrinkage compensation utilizing photosensitive resins.

It relates more specifically, but not exclusively, to a process for filling a dental cavity, and also to a general hand tool for the implementation of the process.

Although this process is adapted for use within the field of dental surgery, numerous other industrial applications for the process in accordance with the invention are readily apparent which involve the wish to partially a cavity arranged in a support of some kind, or to mold an object, or to even cover it with resins capable of photopolymerization.

The invention is described below specifically with reference to the field of application which concerns the application and subsequently the solidification of an initially pasty product within a dental cavity.

The invention may similarly be applied to other industrial areas, for example to those involving precision molding and casting, and more particularly to the process known as the "lost wax" casting process which is used, for example, with items of small dimension.

BACKGROUND OF THE INVENTION

By way of summary, in the dental field of application which has been taken as an example, the treatment of dental caries in particular by the direct method is frequently performed by the use of a compound resin or of an amalgam which the dental practitioner deposits within the previously cleaned cavity, with solidification of the amalgam being achieved by setting and/or by means of the microretentions situated upon the walls of the cavity.

In the case of an anesthetic compound resin, hardening is achieved by means of polymerization with the addition of a chemical substance, or by means of electromagnetic radiation.

With regard to the latter case, the process currently in use involves, after first having cleaned the walls of the dental cavity to be treated, depositing in a number of successive layers a mass of photosensitive compound resin intended to fill the cavity, and then carrying out hardening, layer by layer, by means of photopolymerization of the resin as a result of the use of electromagnetic radiation such as, for example, luminous radiation emitted by means of a light source, the wavelength of which corresponds to the reaction for the initiation and solidification of the resin.

This photopolymerization process offers appreciable advantages in relation to the customary chemical techniques which are still being practiced at this time, since it no longer requires rapid intervention on the part of the dental practitioner as a consequence of the short setting time of the hardener.

These disadvantages characteristic of the customary chemical techniques also do not exist in the method which uses a photosensitive resin, since the photopolymerization reaction of the viscous resin does not commence until the moment the same is activated by means of the radiation triggered by means of the dental practitioner.

It has been found, however, that certain patients treated by means of this method experienced acute pain because the resin adheres to the walls of the tooth, in particular to the walls of the pulpar chamber where the nerves and the blood vessels are situated, placing them under strain as the resin shrinks. In addition the polymerization, which is always incomplete at the base of the cavity, leaves behind free monomers at that point which are toxic to the dental pulp.

In the case of industrial applications, for example in the field of precision molding, this shrinkage phenomenon, which is well known to the professionals, represents a distinct disadvantage in that it is detrimental to the quality and the precision of the molded and the moulded surfaces.

OBJECT OF THE INVENTION

The object of the present invention is to overcome these disadvantages and concerns a differential photopolymerization process with shrinkage compensation for precision molding and for filling a dental cavity in a single operation based upon the use of resins capable of photopolymerization, and wherein further, the process avoids the walls of the tooth being stressed during hardening of the resin and ensures the complete photopolymerization of the resin.

SUMMARY OF THE INVENTION

With this in mind the process of molding or of filling a dental cavity, of the type in which a photosensitive resin intended to be solidified by means of photopolymerization is deposited in a cavity or within a mold is remarkable in accordance with the invention in that:

a layer of a first photosensitive resin is deposited upon the walls of the cavity or mold, a mass of a second photosensitive resin filling the rest of the cavity is then deposited, on top of the layer of the first photosensitive resin;

the hardening of the mass is performed by means of photopolymerization; and then, after hardening of the mass, the hardening of the layer of the first photosensitive resin is performed.

Thus, in accordance with the invention, the shrinkage which occurs during hardening of the mass of the second photosensitive resin, which occupies the major part of the volume defined by means of the cavity or the mold, does not act directly upon the actual walls of the cavity or the mold, since the layer of the first resin, which has been deposited between these walls and the mass of resin, is still viscous and accordingly acts as a buffer layer. Only after hardening of the mass has taken place does the hardening of the layer of the first resin take place, the small thickness of which, deposited upon the walls of the cavity, does not exercise sufficient tractive forces upon the walls, during its solidification, to cause pain or dimensional variations in shape or surface area.

Furthermore, the first and the second resins each reacts at a level of electromagnetic polymerization radiation of optimum and specific wavelength, that is:

the two resins are preferably selected so that the radiation intended to produce photopolymerization of the mass of the second resin has no effect upon the layer of the first resin;

electromagnetic radiation corresponding to the optimum photopolymerization wavelength of the second resin is then applied to the entire mass of the two resins which have been deposited within the cavity; then after hardening of the second resin, the electromagnetic radiation of optimum wavelength appropriate to the photopolymerization of the first resin is applied.

Thus, the process in accordance with the invention involves performing the differential polymerization of the resins, enabling a major reduction in shrinkage to be achieved.

In addition, prior to deposition of the layer constituted by means of the first photosensitive resin, and after having prepared the cavity of the tooth or the mold with an acid gel, the walls of the cavity or the mold are coated with a bonding agent permitting the resin to bond with the walls.

The present invention also relates to a hand tool intended for the implementation of the process.

For this purpose the hand tool in accordance with the invention, of the type consisting of an essentially tubular body exhibiting a head at one end, is characterized in that it comprises, within the body, means for the transmission of luminous electromagnetic radiation emitted by means of a light source capable of being attached to the other end of the body, which means of transmission emerges from the head in order to penetrate the resins deposited within the cavity, in such a way that, as a function of the adjustable wavelength of the emitted radiation, the hardening by photopolymerization of each of the photosensitive resins is obtained.

In one preferred embodiment, the means for the transmission of the radiation comprises an optical fibre housed within the tubular body and connected at one end to the light source, and a disposable photo-distributing pellet retained within the head and partly emerging from it, which pellet, which receives and transmits the radiation emitted by means of the optical fibre, is capable of being introduced into the resins deposited within the cavity. Thus, once the emergent part has been inserted into the vicinity of the base of the dental cavity or the mold containing the resins, the light source controlled by means of the dental practitioner emits electromagnetic radiation, the wavelength of which corresponds to the photopolymerization reaction of the second resin but does not have any effect upon the layer constituted by means of the first resin, which consequently remains viscous, and in so doing compensates for the reduction in volume of the mass of the second resin. After total hardening of the second resin mass, electromagnetic radiation emitted by means of the light source, the wavelength of which in this case corresponds to the polymerization reaction of the first resin, permits the solidification of the latter, with the emergent part of the pellet being held captive within the solidified mass of the second resin.

Once hardening of the first resin has been achieved, the pellet is released from the tool and is then cut level with the upper surface of the tooth or the mold.

The treatment or molding process is then finished by means of a polishing operation.

A photoelectric cell is advantageously provided upon the head, being so arranged as to face toward the resins. The cell, which is connected to the light source, thus permits the wavelength of the emitted electromagnetic radiation to be varied, by means of an electronic control device, when the opacity of the second resin, which is modified during the solidification process as it transforms from the pasty state to the solid state, corresponds to the total hardening of this resin.

Furthermore, in order to facilitate the operation involved in attaching and removing the disposable pellet to and from the tool, the pellet is inserted by force into a drilled bore formed within the head.

In addition, since one part of the pellet forms one piece with the resins, this is preferably made of a translucent resin, the characteristics of which are compatible with those of the resins deposited within the cavity.

In a preferred embodiment, an optical means for focussing the electromagnetic radiations is arranged between the outlet from the optical fibre and the pellet, whereby the latter, being arranged transversely in relation to the direction of the optical fibre, comes into contact with a reflector fixed to the head. Advantages are to be had from the arrangement of an element within the head and surrounding the pellet, which piezo-electric element generates vibrations whose effect is to consolidate the resins by means of the pellet.

Finally, according to another characteristic of the invention, in order to provide cleaning of the treated tooth or of the precision mold, as well as of the adjacent parts, pipes for the supply of air and for the supply of water respectively may be attached to the body.

BRIEF DESCRIPTION OF THE DRAWING

The Figures comprising the accompanying drawings are intended to illustrate how the invention may be executed in the case of an application within the dental field. More particularly, various other objects, features, and attendant advantages of the present invention will become better understood from the following detailed description when considered in conjunction with the accompanying drawings, in which like reference characters designate like or corresponding parts throughout the several views, and wherein.

DETAILED DESCRIPTION OF THE ILLUSTRATED EMBODIMENTS

Figure 1:
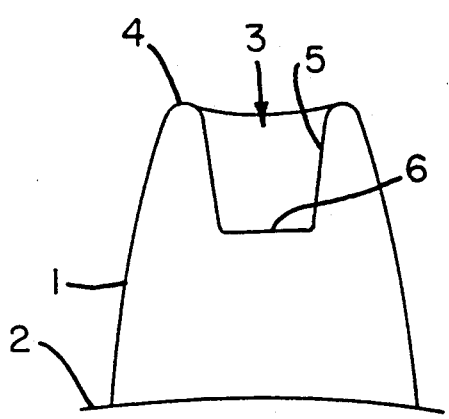
FIGS. 1, 2, 3, 4 and 5 illustrate in diagrammatic form the various stages of the process in accordance with the invention intended for filling a cavity or a mold.

The process illustrated by FIGS. 1 to 5 involves filling a cavity arranged within a tooth or within a molding, although other different or similar applications may be addressed by means of the present invention.

The diagrammatic form represented in the Figures illustrates equally well a tooth viewed in section and a precision mold.

For the purposes of the following description, we shall imagine that the shape represented is that of a tooth. It could equally well be that of a precision mold.

The process of polymerization in accordance with the invention applied to the cavity of a tooth is described below. The same process can be applied equally well to any other cavity, in particular that of a precision mold.

A tooth 1 disposed within the gum 2 exhibits a cavity 3 which opens, for the purposes of this example, in the occlusive surface 4 of the tooth and is defined by means of its lateral walls 5 and its base 6.

Figure 2:
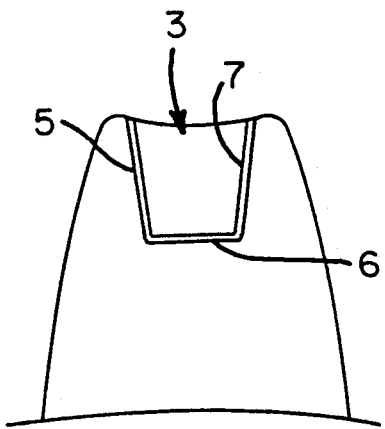

The dental practitioner proceeds beforehand to clean in particular the walls 5 and the base 6 of the cavity 3 in a previously disclosed manner. After having treated the enamel of the cavity with an acid gel, he then coats, as shown in FIG. 2, the lateral walls 5 and the base 6 with a bonding agent 7 or an adhesive intended to cause the resins to bond, as will be seen later, with the walls and the base of the cavity 3 of the tooth or the mold, which bonding agent may be an amelodentinocene.

Figure 3:
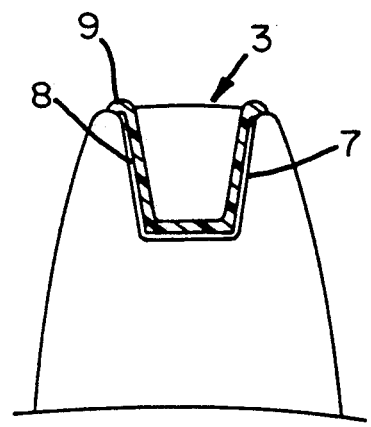

He then deposits, as shown in FIG. 3, onto the bonding agent 7, a layer 8 of a first photosensitive resin of a previously disclosed type. The layer 8 overflows from the cavity 3 of the tooth or the mold, as shown in an accentuated manner in FIG. 3, in such a way that a lateral edge 9 of the layer 8 rests upon the masticatory surface 4 of the tooth.

Figure 4:
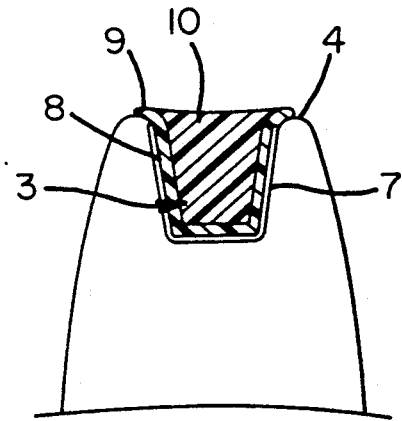

The dental practitioner then deposits onto the layer 8, as shown in FIG. 4, a mass 10 of a second photosensitive resin, and in so doing essentially fills the rest of the cavity 3 of the tooth or the mold. The volume of the deposited mass 10 of the second resin corresponds approximately to the volume of the cavity 3 of the tooth or the mold to be filled.

Each of the first and second photosensitive resins constituting respectively the layer 8 and the mass 10 is selected so that it will react with electromagnetic polymerization radiation levels of optimum specific or retardative wavelengths. Thus, the first photosensitive resin will react under the influence of electromagnetic radiation whose wavelength corresponds to the hardening by polymerization of this first resin, whereas the second resin will react under the influence of electromagnetic radiation whose wavelength, unlike that which initiates the first resin, corresponds to the hardening by photopolymerization of this second resin.

The dental practitioner then carries out the hardening by polymerization of the mass 10 of the second photosensitive resin, which, under the influence of the electromagnetic radiation, for instance of the luminous type, transforms from a viscous state to a solid state. During the solidification phase of the second resin the first photosensitive resin is still in a viscous state, since it does not react to the electromagnetic radiation of the specific wavelength corresponding to the photopolymerization of the second resin. The layer 8 thus acts as an intermediate buffer layer between the second resin and the walls of the tooth or mold. The reduction in the volume of the mass 10 of the second resin is compensated for by means of the layer 8 of the first resin, and in so doing produces differentiated shrinkage, since the excess of the latter as defined by means of the lateral edge 9 deposited upon the surface 4 of the tooth or the mold then flows between the solidified mass 10 and the coating of bonding agent 7. As a consequence of this the mass 10 is totally isolated from the walls and from the base of the cavity 3, and in particular from the pulp chamber in the case of a tooth, whereby the nerves situated in the chamber are not affected.

After the total hardening of the second resin the dental practitioner then performs, by means of electromagnetic radiation of a specific wavelength (different from that corresponding to the initiation of the second resin), the hardening by photopolymerization of the layer 8 of the first resin. Due to the small thickness of the layer 8 deposited upon the walls 5 and upon the base 6 of the dental cavity 3 through means of the coating of bonding agent 7, this fine layer 8 does not exert, during its solidification under the influence of the luminous radiation, sufficient tractive forces upon the walls of the tooth or the mold, and in particular upon the pulpar chamber, to cause any pain. In fact, the volume of the cavity 3 of the tooth or the mold is filled practically in its totality by the already solidified mass 10.

Figure 5:
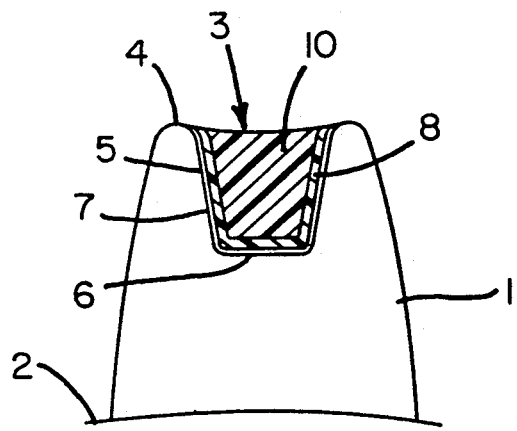

Then, once the layer 8 is completely solidified and is bonded to the walls 5 and to the base 6 of the cavity 3 as a result of the coating of bonding agent 7, the dental practitioner carries out fettling, polishing and cleaning operations upon the surface of the hardened resins, in order to cause this surface to conform to that defined by means of the masticatory surface 4 (FIG. 5).

Photopolymerization of the kind known as differential photopolymerization is achieved in this way, as a result of the process to which the invention relates, which process eliminates by compensation the tractive forces which are normally exerted upon the walls of the cavity, and which are due to the shrinkage in volume of the photosensitive resins during the course of the solidification process.

The invention also relates to a hand tool for the implementation of the process described above.

Figure 6:
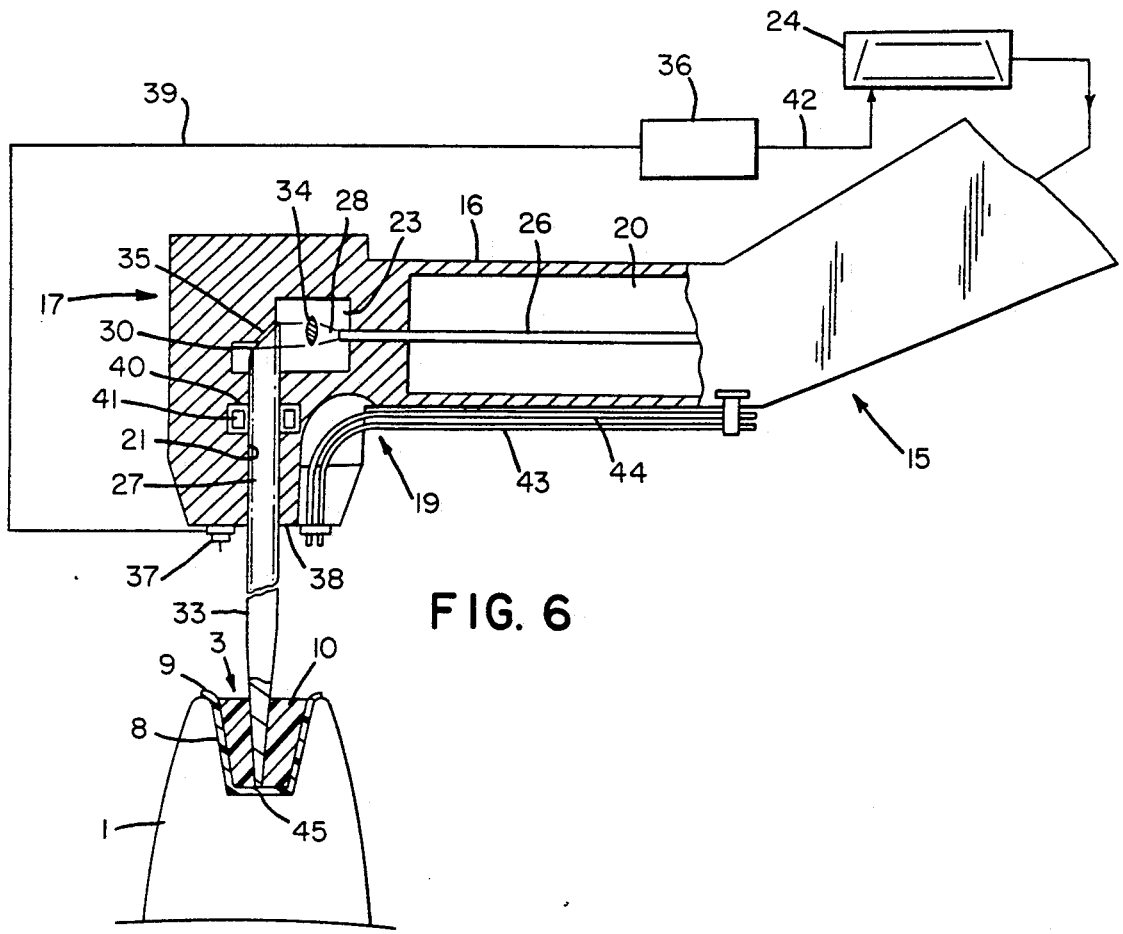
FIG. 6 represents, in partially sectioned and diagrammatic form, a hand tool in accordance with the invention intended for the implementation of the process, the tool being shown at the stage of the process corresponding to the photopolymerization of the resins.

The hand tool 15, shown in FIG. 6, comprises a body 16 essentially of tubular form having a head 17 at one extremity 19, with the other extremity of the body 16 not being illustrated. The tubular body has an internal passageway 20 opening into a drilled bore 21 formed within the head 17 and having a direction perpendicular to that of the passageway 20.

Means 23 for the transmission of luminous electromagnetic radiation emitted by means of a light source 24 are disposed within the body 16. These means 23 are linked, by means of that extremity of the body 16 which is not illustrated, to the light source 24, irrespective of whether or not this is coherent, such as an argon laser, for example. These means project beyond the head 17 in order to penetrate, as will be seen later, into the differentially activated photosensitive resins which are deposited within the dental cavity 3 or within the mold.

In this embodiment the means 23 are comprise by an optical fibre 26 and a photo-distributing pellet 27 formed from a translucent material.

The extremity of this pellet has a form such that it permits the uniform distribution of luminous energy into the entire volume occupied by means of the second resin, that is to say the mass 10. In addition, this form of the extremity should enable the formation of bubbles to be avoided at the time of its penetration into the mass 10.

This pellet is disposable, that is to say it is embedded, as will be seen later, with its end remaining permanently within the mass 10 of resin. Its essential role is to uniformly distribute the energy from the luminous radiation, so as to obtain the best possible polymerization effect inside the volume into which it is inserted. The optical fibre 26 is housed and retained inside the internal passageway 20 of the body 16 and is attached by means of its inlet, not shown here, to the light source 24, whereas the outlet 28 from the optical fibre is disposed toward the drilled bore 21, with the optical fibre itself being arranged in a direction essentially perpendicular to the latter. The pellet 27, for its part, is disposed within the drilled bore 21 and, in this particular embodiment, is inserted by force into the latter. The pellet 27 has an extremity 33, for example of cylindro-conical form, which emerges from the head 17.

Additionally provided within the tool 15 are, on the one hand, an optical means for focussing, such as, for example, a lens 34 arranged between the outlet 28 from the optical fibre 26 and the pellet 27, and, on the other hand, a reflector 35 disposed toward the lens 34 and inclined at an angle of 45°. The pellet 27 rests by means of one extremity, which is cut so as to have an inclined face 30, against the reflector 35, in such a way that, once luminous radiation has emerged from the outlet 28 of the fibre, it is focussed by means of the lens 34 and is then reflected by means of the reflector 35 in the axial sense along the pellet 27.

A photo-electric cell 37 is fixed to the face 38 of the head 17, in such a way as to be directed so that it faces the resins deposited within the cavity 3. This cell 37 is connected by means of a link 39 to an electronic control device 36, which is itself connected by means of a link 42 to the light source 24. Also provided within the drilled bore 21 within the head 17 is an annular groove 40 intended to accommodate a piezo-electric element 41. The functions of the cell 37 and of the piezo-electric element 41 are described below.

Finally, pipes for the supply of water 43 and for the supply of air 44 respectively are fixed to the body 16, with each outlet orifice discharging upon a level which is co-planar with the face 38 of the head 17.

The dental practitioner positions the disposable pellet 27 within the drilled bore 21 within the head, in such a way that the inclined face 30 comes to rest correctly against the reflector 35. The pellet, which is inserted by force, is formed from in a translucent resin compatible with those previously deposited within the cavity 3, or, in another embodiment, the pellet may be formed from a cast glass.

The tool 15 is connected by means of the optical fibre 26 to the light source 24. After switching on the latter, the dental practitioner inserts the emergent cylindro-conical part 33 of the pellet 27 into the mass 10, in such a way that the face at its extremity 45, which is perfectly polished, is situated within the vicinity of the base 6 of the cavity 3 containing the mass 10 of second resin and the layer 8 of first resin. The light source 24, controlled by means of the dental practitioner, then emits, after selection of filtering or otherwise, electromagnetic radiation corresponding to one of the colors of the visible spectrum. The wavelength of the luminous radiation corresponds to the photopolymerization reaction of the mass 10 of the second resin. This luminous radiation then passes along the optical means 23, that is to say the optical fibre 26, through the focussing lens 34, and is then reflected by mean of the reflector 35 in the direction of the pellet 27, to be discharged by means of the end face 45 of the emergent end 33 of the pellet 27 into the photosensitive resins.

The photopolymerization reaction of the mass 10 of the second photosensitive resin then begins.

Advantages are to be gained from the fact that the piezo-electric element 41 generates vibrations transmitted by means of pellet 27 to the mass of resins, the effect of such vibrations being to significantly compact the mass of the second resin. During the change in state of the latter, as it transforms from a pasty or viscous state into a solid state, a variation occurs in the opacity of the mass 10 of the second resin. This variation in opacity is detected by means of the photo-electric cell 37. Thus, when the opacity of the mass 10 of the second resin corresponds to that of its total solidification, the photo-electric cell 37 will emit a signal, transmitted by means of the link 39, to the electronic control device 36 connected to the light source 24. This control device automatically triggers the change or modifies the selection of the wavelength of the emitted luminous radiation. The new, specific wavelength, either in service or selected, then corresponds to the photopolymerization reaction of the layer 8 of the first photosensitive resin and changes color accordingly.

The first resin, which isolates the mass 10 of the second resin from the walls and from the base of the cavity, hardens until total solidification occurs.

During this process the activation energy intended for the photopolymerization of the mass of the second resin is less than the activation energy intended for the photopolymerization of the layer of the first resin.

The dental practitioner interrupts the function of the light source 24. The emergent extremity 33 is then partially held captive within and is bonded to the mass 10 of the second resin.

The dental practitioner then releases the disposable pellet 27 from the hand tool 15, at which point the pellet 27 is partly inserted within the hardened resins. With the help of cutting pliers or a similar tool, the dental practitioner then cuts off the emergent part of the pellet flush with the upper surface of the tooth. Next, a conventional fettling operation, followed by means of a polishing operation, is performed so as to complete the treatment. Cleaning of the tooth and its adjacent parts is afforded by means of the pipes for the supply of air 44 and water 43.

Figure 7:
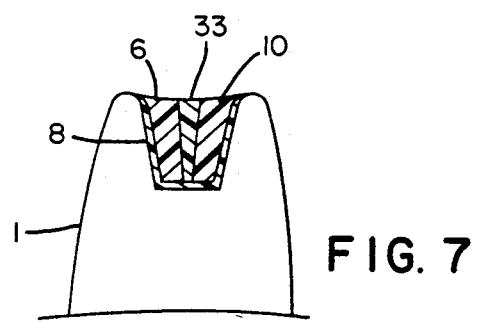
FIG. 7 is a diagrammatic sectioned view of a tooth treated in accordance with the process to which the invention relates by means of the hand tool provided for this purpose.

The tooth treated in this way, or the mold filled by means of the process to which the invention relates, and achieved by means of the special tool, are illustrated in diagrammatic form in FIG. 7.

The use of two resins capable of auto-calcination and photo-polymerization at two luminous radiation values with different wavelengths enables applications in the field of precision casting to be achieved. In fact, since the auto-calcinable resins which are currently available do not leave any apparent residue, the use of the casting or molding process known as the "lost wax" process enables hollow forms, especially in the case of items of small dimensions, to be produced to great accuracy, as a result of the present invention.

Obviously, many modifications and variations of the present invention are possible in light of the above teachings. It is therefore to be understood that within the scope of the appended claims, the present invention may be practiced otherwise than as specifically described herein.

I claim:

1. A process of filling a cavity with photosensitive resin materials which are capable of being solidified by means of photopolymerization, comprising the steps of:
    depositing a layer of a first resin material, which is photosensitive at a first predetermined level of luminous radiation, upon the walls of said cavity;
    subsequently depositing a mass of a second resin material, which is photosensitive at a second predetermined level of luminous radiation which is different than said first predetermined level of luminous radiation, upon said layer of said first resin material;

subsequently exposing said first and second resin materials to said luminous radiation at said second predetermined level so as to harden only said second resin material by photopolymerization; and subsequently exposing said first and second resin materials to said luminous radiation at said first predetermined level so as to harden said first resin material by photopolymerization.

2. The process as set forth in claim 1, wherein:
said first and second levels of luminous radiation are applied to said first and second resin materials by means of a luminous radiation transmitter which is partially embedded within said second resin material.

3. The process as set forth in claim 1, wherein:
prior to said deposition of said first resin material upon said walls of said cavity, said walls of said cavity are coated with a bonding agent.

4. The process as set forth in claim 1, wherein:
said first and second resin materials are photosensitive to predetermined different levels of said luminous radiation such that said luminous radiation of said second predetermined level for hardening only said second resin material is ineffective with respect to said polymerization of said first resin material whereby said first resin material is not polymerized by said second predetermined level of said luminous radiation.

5. A hand tool for implementing photopolymerization of two different photosensitive resin materials which are disposed within a cavity wherein a first one of said two resin materials is deposited upon the walls of said cavity, and a second one of said two resin materials is deposited within said cavity and upon said first one of said two resin materials, comprising:
means, defined within said hand tool, for receiving electromagnetic radiation at one end thereof from a light source, and for transmitting said electromagnetic radiation to an opposite end thereof which is insertable within said resin materials disposed within said cavity; and
means for controlling the level of said electromagnetic radiation issued from said light source so as to generate electromagnetic radiation at a first predetermined level to which both said first and second resin materials will be exposed but by which only said second one of said two resin materials will be hardened by photopolymerization, and for generating electromagnetic radiation at a second predetermined level, in response to completion of of said photopolymerization of said second one of said two resin materials, to which both said first and second resin materials will be exposed but by which only said first one of said two resin materials wil be hardened by photopolymerization.

6. The hand tool as set forth in claim 5, wherein said means for receiving and transmitting said electromagnetic radiation, comprises:
an optical fiber having one end thereof optically connected to said light source, and a light-transmissive pellet having one end thereof optically connected to a second end of said optical fiber, while a second end of said light-transmissive pellet is insertable within said resin materials disposed within said cavity.

7. The hand tool as set forth in claim 6, wherein:
a longitudinal axis of said optical fiber is disposed substantially perpendicular to a longitudinal axis of said light-transmissive pellet.

8. The hand tool as set forth in claim 7, further comprising:
a lens interposed between said one end of said light-transmissive pellet and said second end of said optical fiber; and
a reflector, disposed at an angle of 45° with respect to said longitudinal axes of said optical fiber and said light-transmissive pellet, interposed between said lens and said one end of said light-transmissive pellet.

9. The hand tool as set forth in claim 6, further comprising:
piezoelectric means operatively associated with said light-transmissive pellet for generating vibrations transmitted by said light-transmissive pellet to said resin materials for compacting said resin materials during said photopolymerization of said first and second resin materials.

10. The hand tool as set forth in claim 6, further comprising:
photoelectric sensor means mounted upon said tool and disposed toward said resin materials disposed within said cavity for sensing the opacity of said second resin material upon said completion of said photopolymerization of said second resin material and for generasting a control signal to said means for controlling the level of said electromagnetic radiation issued from said light source so as to change said electromagetic radiation from said first predetermined level to said second predetermined level.

11. The hand tool as set forth in claim 6, further comprising:
conduit means secured to said hand tool for transmitting air and water toward said cavity and said resin materials disposed therein.

* * * * *